United States Patent [19]
Fukushima et al.

[11] Patent Number: 5,391,221
[45] Date of Patent: Feb. 21, 1995

[54] GAS CHROMATOGRAPH AND METHOD OF USING SAME

[75] Inventors: Toyoaki Fukushima; Kazuya Nakagawa; Masahito Ueda; Satoru Miyoshi, all of Kyoto, Japan

[73] Assignee: Shimadzu Corporation, Kyoto, Japan

[21] Appl. No.: 34,677

[22] Filed: Mar. 19, 1993

[30] Foreign Application Priority Data

Apr. 6, 1992 [JP] Japan ............................ 4-114160

[51] Int. Cl.⁶ ............................................ B01D 15/08
[52] U.S. Cl. ............................................ 95/82; 95/89; 96/102; 96/105
[58] Field of Search ............... 73/23.35, 23.36, 23.41, 73/23.42; 95/82–87, 89; 96/101–106

[56] References Cited

U.S. PATENT DOCUMENTS

| | | | |
|---|---|---|---|
| 2,813,010 | 11/1957 | Hutchins | 73/23.35 X |
| 3,357,233 | 12/1967 | Roof | 73/23.42 |
| 3,881,892 | 5/1975 | Gehrke et al. | 96/103 X |
| 3,985,016 | 10/1976 | Haruki | 73/23.35 X |
| 4,124,358 | 11/1978 | Müller | 95/83 |

OTHER PUBLICATIONS

H. Bruderreck et al., "Quantitative Gas Chromatography Analysis of Hydrocarbons with Capillary Columns and Flame Ionization Detector, IV Principle of a New Splitting System", J. of Gas Chromatography, May, 1967, pp. 217–225.

*Primary Examiner*—Robert Spitzer
*Attorney, Agent, or Firm*—Heller, Ehrman, White & McAuliffe

[57] ABSTRACT

A gas chromatograph for operation selectably in both split mode and splitless wide bore injection mode includes a capillary column, a sample injection chamber at the inlet of the column, a three-way valve, a first piping line connected between one of the two outlets of the three-way valve and the sample injection chamber, a split line connected to the sample injection chamber immediately upstream of the inlet of the column for discharging therethrough a portion of a gas being sent out from the sample injection chamber, a second piping line connected between the other of the outlets of the three-way valve and the split line, and a third piping line connected between the first and second piping lines. By properly controlling the total carrier gas flow rate and the column inlet pressure, the split ratio can be controlled easily. By varying the split ratio appropriately during an analysis, the amount of the carrier gas to be wasted in the case of a split mode of operation can be significantly reduced.

12 Claims, 2 Drawing Sheets

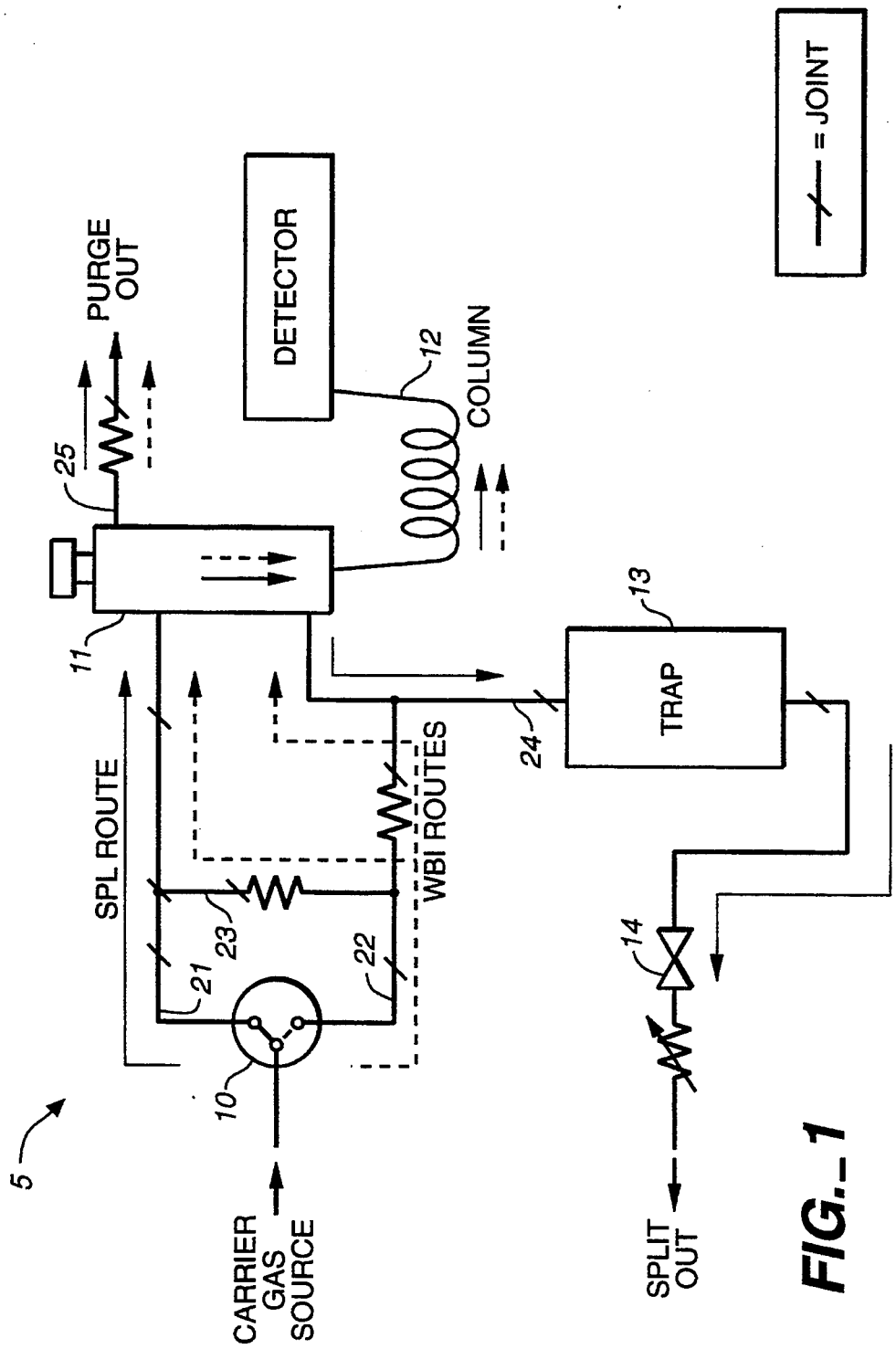
FIG._1

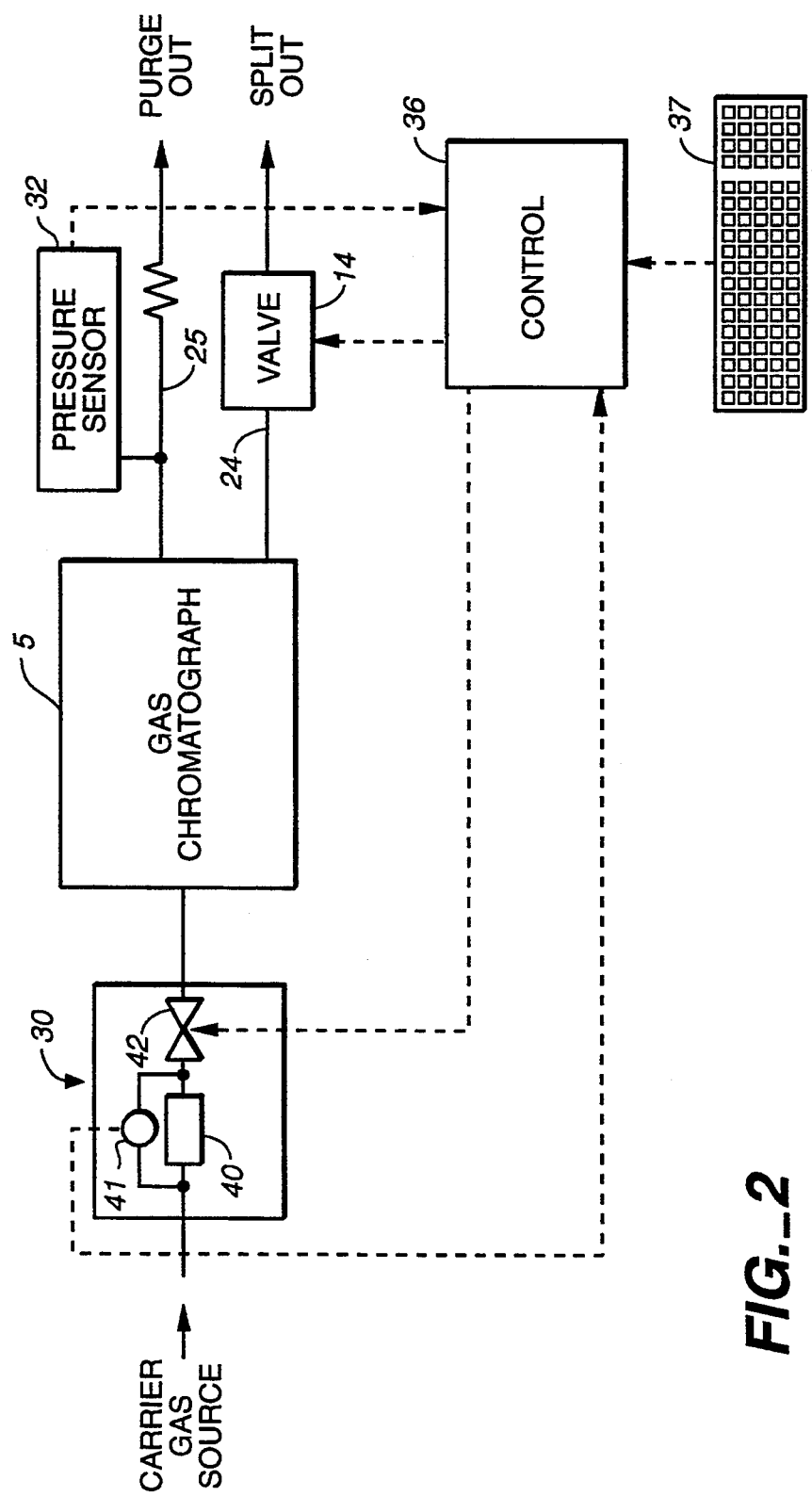
FIG._2

GAS CHROMATOGRAPH AND METHOD OF USING SAME

BACKGROUND OF THE INVENTION

This invention relates to a gas chromatograph and a method of using it selectably in split and wide bore injection modes.

When high accuracy gas chromatographic analyses are desired, it has been known to use a gas chromatograph in a so-called split mode wherein the injected sample is split and only a fraction thereof is introduced into the capillary column.

When it is desired to detect a component which is contained only by a small quantity, on the other hand, a so-called wide bore injection analysis is much more suitable for accurate analysis. In a wide bore injection analysis, therefore, a splitless injection is more often applied than the split injection. Thus, prior art apparatus for gas chromatography were provided separately with both a unit for split mode analyses and another unit for wide bore injection analyses. Whenever the mode of analysis was to be changed with such an apparatus, these units including both a column and a sample injection chamber had to be exchanged and the pipes reconnected.

Sample injection chambers for use in a wide bore injection analysis are distinguishable from those for use in a split mode analysis only in that there is no split piping line connected thereto. It may be thought, therefore, that a sample injection chamber for split mode analysis can be used for a wide bore injection analysis simply by blocking the split piping line such that the sample will not split out therethrough. This, however, is not so for the following reasons. Firstly, since sample injection chambers and columns are generally unitized, the valve to be used for blocking the split line must be located near its outlet. Secondly, the split piping line must be provided with a trap for removing the sample from the gas which is being split out. For the reason mentioned above, there results a relatively large dead space between the sample injection chamber and the valve for blocking the split piping line. In a wide bore injection analysis, a relatively large part of the sample tends to accumulate and stay in this dead space, failing to be transported into the column. This is the reason why the units as a whole had to be exchanged and the pipes reconnected in the case of a prior art gas chromatographic apparatus whenever the mode of analysis was switched between the split mode and the wide bore injection mode.

The present invention was accomplished in view of this problem. In other words, it is an object of the present invention to provide a gas chromatograph which can be easily switched between a split mode analysis and a wide bore injection analysis.

SUMMARY OF THE INVENTION

A gas chromatograph according to the present invention, with which the above and other objects can be accomplished, may be characterized as comprising (a) a sample injection chamber connected to the column inlet for injecting a sample into a carrier gas; (b) a first piping line connecting a carrier gas source with the sample injection chamber; (c) a split line connected to the sample injection chamber immediately upstream of the column inlet for discharging therethrough a portion of the gas being sent out from the sample injection chamber; (d) a three-way valve with an inlet connected to the carrier gas source and one of its outlets connected to the first piping line; and (e) a second piping line connecting the other outlet of the three-way valve and the first piping line and having a branch to the split line.

For a split mode analysis, the three-way valve is switched to the first piping line such that the carrier gas from its source flows through the three-way valve, the first piping line and the sample injection chamber into the column and the split line. The sample, which is injected into the sample injection chamber, is in part sent into the column and in part discharged through the split line.

In the case of a wide bore injection analysis, the three-way valve is switched to the second piping line such that the carrier gas from its source flows through the following two routes to be introduced into the sample injection chamber, the first route extending from the three-way valve through the second piping line and the first piping line to the sample injection chamber, and the second route extending from the three-way valve through the second piping line and the split line to the sample injection chamber. Thus, the sample, which is injected into the sample injection chamber, is entirely sent into the column without entering the split line.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a piping diagram of a gas chromatograph embodying the present invention; and FIG. 2 is a block diagram of a control system for the gas chromatograph of FIG. 1.

DETAILED DESCRIPTION OF THE INVENTION

FIG. 1 illustrates a gas chromatograph 5 according to one embodiment of the present invention which can be used selectably both for a split mode analysis and for a wide bore injection mode merely by exchanging columns and making a switch on a valve.

As shown in FIG. 1, a sample injection chamber 11 is disposed at the inlet of a column 12, and a first piping line 21 for introducing a carrier gas from its source (not shown), a split line 24 and a purge line 25 are connected to the sample injection chamber 11. The first piping line 21 connects the sample injection chamber 11 with one of the two outlets of a three-way valve 10, and a second piping line 22 is connected between the other outlet of the three-way valve 10 and the split line 24. There is a third piping line 23 branching from a mid-point in the second piping line 22 and connecting to the first piping line 21. The split piping line 24 includes a buffer 13 containing a filter. The split line 24 includes an electromagnetic valve 14 near its outlet distal from the sample injection chamber 11.

When the gas chromatograph 5 shown in FIG. 1 is used for a split analysis, the three-way valve 10 is switched to the first piping line 21 and the electromagnetic valve 14 in the split line 24 is opened. This causes the carrier gas from the source to be introduced into the sample injection chamber 11 through the inlet of the three-way valve 10 and the first piping line 21, as indicated by a solid arrow marked "SPL route" in FIG. 1.

After a sample is injected into the sample injection chamber 11, a portion of the mixture (that is, the injected sample and the carrier gas) is directed to the column 12 to be analyzed by means of a detector. Another portion is directed into the split line 24 from the sample injection chamber 11, passed through the trap 13 and discharged (or split out). The sample material in the gas in the split line 24 is captured by, the filter in the trap 13 so as not to contaminate the electromagnetic valve 14 or the external environment. A portion of the carrier gas introduced into the sample injection chamber 11 is directed towards the rubber plug for the sample inlet (at an upper part of the chamber 11 in FIG. 1) so as to carry away the unwanted contaminants from the rubber material of the plug and to have them purged out from the purge line 25.

When the gas chromatograph 5 shown in FIG. 1 is used for a wide bore injection analysis, the three-way valve 10 is switched to the second piping line 22 and the electromagnetic valve 14 in the split line 24 is closed. This causes the carrier gas from the source to be introduced into the sample injection chamber 11 through two routes, as indicated by broken arrows marked "WBI routes" in FIG. 1. One of the WBI routes passes through an upstream portion of the second piping line 22, the third piping line 23 and a downstream portion of the first piping line 21 to the sample injection chamber 11. The other passes through the second piping line 22 and a portion of the split line 24 to the sample injection chamber 11. Since the gas resistance is approximately the same between these two routes, the carrier gas, which has been introduced into the sample injection chamber 11 and into which a sample has been injected, does not leave the chamber 11 through the split line 24. In other words, the injected sample is entirely transported into the column 12 for a wide bore injection analysis.

Next, FIG. 2 will be referenced to describe methods of the present invention for operating the gas chromatograph 5 of FIG. 1 such that the split ratio (defined as the ratio between the flow rates of gas through the column 12 and the split line 25 when the gas chromatograph is operated in a split mode) can be easily adjusted and the amount of the carrier gas to be wasted can be reduced. For convenience, detailed structure of the gas chromatograph 5 itself is not shown in FIG. 2. Numeral 30 indicates a mass flow controller, connected to the inlet of the three-way valve 10, for adjusting the total carrier flow gas flow rate U from its source (not shown) into the gas chromatograph 5. It may be of a known structure, including a laminar flow control 40, a differential pressure sensor 41 and a flow rate control valve 42 for determining and adjusting the flow rate U to a specified value $U_0$. Numeral 32 indicates a pressure sensor in the purge line 25. Since there is hardly any gas resistance between this pressure sensor 32 and the sample injection chamber 11, the pressure value outputted by the pressure sensor 32 may be considered to represent the column inlet pressure, or the pressure inside the sample injection chamber 11. Numeral 36 indicates a control unit. Various parameters (to be described below) inputted from a keyboard 37, or an external memory device (not shown), are used by the control unit 36 to control each component of the apparatus described above such that the split ratio becomes equal to a specified value. Before the functions of the various components described above for the controlled operation of the gas chromatograph 5, the basic principle of controlling the split ratio according to the present invention will be briefly summarized next.

The gas flow rate inside the column 12 (or the column flow rate $U_c$) depends on the length L and the inner diameter D of the column 12, the gas temperature T and the gas pressure P (which may be represented by the pressure value at the column inlet). This functional relationship may be expressed as:

$$U_c = f(T, D, L, P) \tag{1}$$

The form of the function f(T, D, L, P) can be theoretically derived hydrodynamically, and depending upon the physical properties of the gas being used. Such a function may be derived also by experimentally determining various coefficients of a hydrodynamically derived basic formula.

Since the physical dimensions (length, inner diameter, etc.) and temperature of the purge line 25 are constant, the flow rate therethrough (the purge flow rate) $U_p$ depends only on the gas pressure P and may be expressed as:

$$U_p = g(P) \tag{2}$$

where the function g(P) can be derived in a similar manner as the aforementioned function f(T, D, L, P). The split flow rate $U_s$ (or the gas flow rate through the split line 24) is related to the column flow rate $U_c$ and the split ratio S as:

$$U_s = S U_c. \tag{3}$$

Since the total carrier gas flow rate U is the sum of the column flow rate $U_c$, the purge flow rate $U_p$ and the split flow rate $U_s$, $$\begin{aligned} U &= U_c + U_p + U_s \\ &= U_c + U_p + S U_c \\ &= (1 + S) f(T, D, L, P) + g(P). \end{aligned} \tag{4}$$

Thus, in order to adjust the split ratio S of this apparatus to a specified value $S_0$ where the length and inner radius of the column 12, temperature and the column inlet pressure are given respectively as $L_0$, $D_0$, $T_0$ and $P_0$, the total flow rate U of the carrier gas should be made equal to $U_0$ given by the following formula:

$$U_0 = (1 + S_0) f(T_0, D_0, L_0, P_0) + g(P_0). \tag{5}$$

In order to accomplish this, the control unit 36 proceeds as follows to adjust the split ratio to a specified value $S_0$. First, the operator inputs from the keyboard 37 the column temperature $T_0$, the length $L_0$ and the inner diameter $D_0$ of the column, a specified value of column inlet pressure $P_0$, and another specified value of split ratio $S_0$. On the basis of these inputted data, the control unit 36 uses Formula (1) to calculate the column flow rate $U_{c0} = f(T_0, D_0, L_0, P_0)$ and Formula (5 to calculate the total flow rate $U_0$ of the carrier gas. Next, the opening of the control valve 14 is adjusted such that the detected value of the pressure P from the pressure sensor 32 will be constant at the specified value $P_0$. As a result, the purge flow rate $U_{p0} = g(P_0)$ becomes constant, making the column flow rate $U_{Uc0} = f(T_0, D_0, L_0, P_0)$ also constant if the temperature is constant. Thus, the split flow rate $U_s$ also becomes constant if the mass flow controller 30 is controlled such that the carrier gas flow rate is $U_0$, and the split ratio of the apparatus is kept constant at the specified value $S_{S0}$.

According to the method of operation described above, the split ratio can be maintained constant, even if there are gradual changes in the column temperature T, by sequentially carrying out the calculations described above on the basis of the temperature at each point in time to thereby update the target pressure value $P_0$ and the carrier gas flow rate $U_0$.

Since the column inlet pressure P can be derived from the average linear column speed $v_m$, it may instead be required to specify an average linear column speed value $V_{m0}$ and a split ratio value $S_0$ from the keyboard 37. More generally, it is to be noted that if any one from the average linear speed $v_m$, the column inlet pressure P and the purge flow rate $U_p$ is set, and if either the total flow rate U or the split ratio S is set, the others of these parameters are uniquely determined. In other words, any combination of one from $v_m$, P and $U_p$ and either U or S may be specified to determine all of them.

Although it was explained above that the values $D_0$ and $L_0$ of the inner diameter and the length of the column 12 were to be inputted from the keyboard 37, this is not intended to limit the scope of the invention. According to an alternative input method, the inner diameters and the lengths of all columns that are expected to be used are preliminarily stored in the control unit 36, and the-user is required only to specify a column, and the required data for the specified column are automatically read out. Similarly, standard values of column input pressure $P_0$ and split ratio $S_0$ may be preliminarily stored in the control unit 36, allowing the user to choose from such standard values. As for the column temperature $T_0$, a preferred method is to cause the temperature data to be automatically inputted into the control unit 36, for example, from the control device for analysis being carried out and in accordance with the mode of this analysis.

Next will be described a few examples of a way in which a gas chromatograph, as described above, may be used. In a first example, the apparatus is used selectably both for a split analysis and a splitless wide bore injection analysis. Conventionally, apparatus for a split analysis and those for a splitless wide bore injection analysis were separately provided. The gas chromatograph described above, however, can be used in a splitless mode by closing the control valve 14 completely and controlling the flow rate control valve 42 of the mass flow controller 30 such that the pressure value P detected by the pressure sensor 32 will become equal to a specified value $P_0$. Thus, if the control unit 36 is preliminarily so programmed that a control as described above will be carried out in response to an input of zero from the keyboard 37 as the value of split ratio $S_0$, or an input of a command for a total flow analysis, the apparatus can be switched between the split and splitless modes of analysis merely by a key input.

Another example is a mode of operation in which the split ratio is intentionally varied during the course of a single analysis such that the amount of carrier gas to be wasted will be reduced. The purpose of a split is to divided into parts the sample injected into the carrier gas, and it is only the carrier gas that is split out before the sample is injected or after the sample has been sent out to the column. This means that a significant amount of the carrier gas is wasted where, for example, the split ratio is 1:100 such that the carrier gas is mostly split out.

According to an embodiment of the present invention, the control unit 36 causes the split ratio S to be varied during a single analysis, as will be explained next.

First, the mass flow controller 30 and the control valve 14 are controlled such that the split ratio-becomes equal to a preliminarily specified value $S_0$ (such as 100), and the injection of sample is started after the flow rate has stabilized. After the sample injection is completed, the split ratio is maintained at the specified value $S_0$ for a selected length of time (such as one minute) which is longer than the time required for sending the sample into the column 12. After this selected length of time, the split ratio is changed to a reduced value $S_1$ (such as 5). In this manner, the amount of carrier gas that is split out can be significantly reduced.

With the gas chromatograph 5 thus controlled according to the present invention, troublesome operations such as the direct measurements of the column flow rate and the split flow rate are not necessary, and split mode analyses can be carried out with an arbitrarily specified split ratio. Moreover, a single apparatus can be used both in split and splitless modes, and the amount of wasted carrier gas can be reduced significantly by appropriately varying the split ratio during the course of an analysis.

What is claimed is:

1. A method of operating a gas chromatograph which includes:

a column with an inlet;

a sample injection chamber at said inlet of said column;

a three-way valve with an inlet, a first outlet and a second outlet, said inlet being connected to a carrier gas source;

a first piping line connected between said first outlet of said three-way valve and said sample injection chamber;

a split line connected to said sample injection chamber immediately upstream of said inlet of said column for discharging therethrough a portion of a gas being sent out from said sample injection chamber;

a second piping line connected between said second outlet of said three-way valve and said split piping line; and a third piping line connected between said first and second piping lines;

said method comprising the steps of:

introducing a carrier gas through said inlet of said three-way valve and entirely through said first outlet thereof into said sample injection chamber at intake flow rate U to thereby cause a portion of said carrier gas to flow through said column at column flow rate $U_c$ and another portion of said carrier gas to be split out at split flow rate $U_s$ through said split line, split ratio being defined as the ratio between said column flow rate $U_c$ and said split flow rates $U_s$;

injecting a sample into said sample injection chamber;

specifying a pressure value $P_0$ and a split ratio value $S_0$;

calculating a column flow rate value $U_{c0}$ corresponding to said pressure value $P_0$ by using a predetermined functional relationship between said column flow rate $U_c$ and pressure at said inlet of said column;

calculating an intake flow rate value $U_0$ corresponding to said pressure value $P_0$, said column flow rate value $U_c0$ and said split ratio value $S_0$ by using a predetermined functional relationship of said intake flow rate U with said pressure at said inlet of said column and said split ratio;

adjusting said pressure at said inlet of said column to said pressure value $P_0$; and adjusting said intake flow rate U of said carrier gas to said intake flow rate value $U_0$.

2. The method of claim 1 wherein said pressure at said inlet of said column is adjusted to said pressure value $P_0$ by adjusting the opening of a control valve provided in said split line.

3. The method of claim 1 wherein said intake flow rate U of said carrier gas is adjusted to said intake flow rate value $U_0$ by controlling a mass flow controller connected to said inlet of said three-way valve.

4. The method of claim 1 wherein said steps of adjusting said pressure at said inlet of said column and said intake flow rate U of said carrier gas are repeated sequentially, such that said split ratio is maintained constant in spite of gradual changes in temperature.

5. The method of claim 1 further comprising the step of operating said gas chromatograph in a wide bore injection mode by blocking said split line near its outlet distal from said sample injection chamber and switching said three-way valve such that said carrier gas is caused to be introduced into said sample injection chamber entirely through said second outlet of said three-way valve.

6. A method of operating a gas chromatograph which includes:
a column with an inlet;
a sample injection chamber at said inlet of said column;
a three-way valve with an inlet, a first outlet and a second outlet, said inlet being connected to a carrier gas source;
a first piping line connected between said first outlet of said three-way valve and said sample injection chamber;
a split line connected to said sample injection chamber immediately upstream of said inlet of said column for discharging therethrough a portion of a gas being sent out from said sample injection chamber;
a second piping line connected between said second outlet of said three-way valve and said split line; and
a third piping line connected between said first and second piping lines;
said method comprising the steps of:
introducing a carrier gas through said inlet of said three-way valve and entirely through said first outlet thereof into said sample injection chamber at intake flow rate U to thereby cause a portion of said carrier gas to flow through said column at column flow rate $U_c$ and another portion of said carrier gas to be split out at split flow rate $U_s$ through said split line, split ratio being defined as the ratio between said column flow rate $U_c$ and said split flow rates $U_s$;
adjusting said split ratio to a specified ratio value $S_O$;
injecting a sample into said sample injection unit;
maintaining said split ratio at said specified ratio value $S_0$ for a specified time interval after the completion of said step of injecting said sample; and
thereafter reducing said split ratio to thereby significantly reduce the amount of said carrier gas flowing out through said split line.

7. The method of claim 6 wherein said step of adjusting said split ratio comprises the steps of:
specifying a pressure value $P_0$;
calculating a column flow rate value $U_{c0}$ corresponding to said pressure value $P_0$ by using a predetermined functional relationship between said column flow rate $U_c$ and pressure at said inlet of said column;
calculating an intake flow rate value $U_0$ corresponding to said pressure value $P_0$, said column flow rate value $U_{c0}$ and said specified ratio value $S_0$ by using a predetermined functional relationship of said intake flow rate U with said pressure at said inlet of said column and said split ratio;
adjusting said pressure at said inlet of said column to said pressure value $P_0$; and
adjusting said in take flow rate U of said carrier gas to said intake flow rate value $U_0$.

8. The method of claim 7 wherein said pressure at said inlet of said column is adjusted to said pressure value $P_0$ by adjusting the opening of a control value provided in said split line.

9. The method of claim 6 wherein said specified time interval is long enough to allow said injected sample to be sent into said column.

10. A gas chromatograph operable selectably both in split and wide bore injection modes, comprising:
a column with an inlet;
a sample injection chamber at said inlet of said column;
a three-way valve with an inlet, a first outlet and a second outlet, said inlet being connected to a carrier gas source;
a first piping line connected between said first outlet of said three-way valve and said sample injection chamber;
a split line connected to said sample injection chamber immediately upstream of said inlet of said column for discharging therethrough a portion of a gas being sent out from said sample injection chamber;
a second piping line connected between said second outlet of said three-way valve and said split line; and
a third piping line connected between said first and second piping lines; said three-way valve serving to receive a carrier gas through its inlet and to be switched so as to direct said carrier gas received thereby selectively through said first outlet and said first piping line into said sample injection chamber or through said second outlet, said second piping line and in part through said third piping line and in part through said split line into said sample injection chamber.

11. The gas chromatograph of claim 10 wherein said first, second and third piping lines and said split line each provide gas resistance therethrough, the gas resistance inside said first, second and third piping lines and said split line is such that there is no flow of gas allowed from said sample injection chamber into said split line when said three-way valve is switched such that said carrier gas is introduced into said second piping line instead of said first piping line.

12. The gas chromatograph of claim 10 wherein said split line contains a control valve which is adapted to be closed when said gas chromatrograph is operated in said wide bore injection mode and opened when said gas chromatograph is operated in said split mode.

* * * * *